United States Patent [19]

Kyi

[11] 3,931,190

[45] Jan. 6, 1976

[54] PREPARATION OF 2-CHLOROPYRIDINE BY HYDROGENOLYSIS

[75] Inventor: Roland R. Kyi, North Haven, Conn.

[73] Assignee: Olin Corporation, New Haven, Conn.

[22] Filed: Mar. 4, 1974

[21] Appl. No.: 447,705

[52] U.S. Cl. .......................... 260/290 HL; 260/290
[51] Int. Cl.² ...................................... C07D 213/61
[58] Field of Search .................................. 260/290

[56] References Cited
UNITED STATES PATENTS 3,355,456  11/1967  Sexton ............................... 260/290

Primary Examiner—Harry I. Moatz
Attorney, Agent, or Firm—Robert L. Andersen; Eugene Zagarella, Jr.

[57] ABSTRACT

A process is provided for the preparation of 2-chloropyridine by the liquid phase hydrogenolysis of 2,6-dichloropyridine in the presence of a selected metal and a strong base.

9 Claims, No Drawings

PREPARATION OF 2-CHLOROPYRIDINE BY HYDROGENOLYSIS

This invention relates to the preparation of 2-chloropyridine by hydrogenolysis. More particularly, this invention involves the selective liquid phase hydrogenolysis of 2,6-dichloropyridine in the presence of a selected metal and a strong base.

A need exists for selectively converting 2,6-dichloropyridine to 2-chloropyridine since the dichloro product is an undesired by-product formed during the production of 2-chloropyridine by the chlorination of pyridine. A number of techniques have been disclosed for the hydrogenolysis of halobenzenes (see U.S. Pat. Nos. 2,725,405, 2,866,828 and 3,595,931) and U.S. Pat. No. 2,502,125 discloses a method for the preparation of monobromopyridine by the reduction of dibromopyridine. However, none of these teachings disclose or suggest the selective hydrogenolysis of 2,6-dichloropyridine to form 2-chloropyridine and more significantly, none suggest the process of this invention.

Now it has been found that 2-chloropyridine can be economically and conveniently prepared by the liquid phase hydrogenolysis of 2,6-dichloropyridine in the presence of zinc metal and a strong base.

The selected metal employed in the reaction of this invention is generally any metal which will react with the selected base material to produce hydrogen and also act as a catalyst. Metals of this type include zinc, iron, cobalt, and aluminum. Zinc and iron are the preferred metals for this reaction with zinc being most particularly preferred. The metal is preferably employed in the form of a finely divided metal such as a fine powder or dust.

The base material used in the process of this invention may be any strong base and more particularly an alkali or alkaline earth metal hydroxide. The preferred hydroxides are sodium, potassium, lithium, cesium, rubidium, calcium and magnesium hydroxide with sodium hydroxide being particularly preferred.

The reaction is carried out using a sufficient quantity of selected metal to produce the required amount of hydrogen or excess thereof. The amount of hydrogen needed is not in itself critical and will depend on the desired degree of conversion of 2,6-dichloropyridine and the reaction time. More particularly, at least 0.25 gram-atoms of selected metal per mole of 2,6-dichloropyridine may be used and preferably a ratio of about 1 to 1 or more of said components is used. The base used will generally be in a liquid form and the concentration can vary widely up to about 75 percent by weight of the basic compound in aqueous solution with the preferred concentration being from about 10 to about 53 percent. The amount of base compound can vary widely with at least 0.1 part by weight of said base per part by weight of 2,6-dichloropyridine being used and preferably from about 1 to about 10 parts by weight of base per part by weight of 2,6-dichloropyridine.

The reaction temperature can vary from about $-10°$ to about $100°C$ and preferably from about $0°$ to about $30°C$. Atmospheric pressure can suitably be employed, but pressures of from about 0.2 atmosphere to about 100 atmospheres and preferably from about 1 to about 10 atmospheres may be used.

While the use of a solvent is not necessary in carrying out the process of this invention, well-known organic solvents which will dissolve the 2,6-dichloropyridine may be used. Solvents of this type include aromatic hydrocarbons such as benzene, toluene and xylene; carbon tetrachloride; chloroform and pyridine with pryidine being a preferred solvent. Further illustrations of useful solvents may be found in "Organic Solvents" edited by Weissburger et al, Vol. VII, 2nd edition, 1955.

It is to be noted that the starting material used in this process is 2,6-dichloropyridine. One common way this material is obtained is as a predominant by-product in the chlorination of pyridine to form chloropyridine and while other forms of the dichloropyridine may also be present in minor proportions, the hydrogenolysis process of this invention is particularly applicable to such mixtures of byproducts. The term 2,6-dichloropyridine as used in the specification and claims is intended to include mixtures of dichloropyridines having the 2,6-dichloropyridine as the predominant or major portion thereof.

The reaction time for this process is not critical and may vary depending on the conditions such as temperature and amount of metal used. Generally, it is desired to run the reaction until nearly all or a significant amount of the 2,6-dichloropyridine has been converted.

It is generally desired to agitate the reaction mixture to keep the two layers thoroughly mixed (when using aqueous solution). Agitation can be provided by using well-known mechanical means.

The following examples are further illustrative of the method of this invention.

EXAMPLE I

A reaction flask was charged with 14 grams of 2,6-dichloropyridine and 106 grams of pyridine and agitated moderately. After all the 2,6-dichloropyridine was dissolved, 100 grams of 50 percent caustic aqueous solution (NaOH) and 13.3 grams of zinc dust were added. The reaction was maintained at about 30°C and 1 atmosphere pressure and samples of liquid were taken periodically and analyzed by vapor phase chromatography as follows:

| Reaction time hours | Conversion of 2,6-dichloropyridine | Yields | | |
|---|---|---|---|---|
| | | 2-chloropyridine | Pyridine | Others |
| 1 | 27% | 54% | 36% | 10% |
| 2 | 51% | 52% | 39% | 9% |
| 3 | 68% | 51% | 39% | 10% |
| 5 | 89% | 51% | 39% | 10% |
| 6 | 94% | 51% | 38% | 10% |

EXAMPLE II

The same procedure as Example I was followed using potassium hydroxide instead of caustic. The results obtained were as follows.

| Reaction time hours | Conversion of 2,6-dichloropyridine | Yields | | |
|---|---|---|---|---|
| | | 2-Chloropyridine | Pyridine | Others |
| 1 | 71% | 34% | 59% | 7% |
| 2 | 96% | 34% | 61% | 5% |
| 3 | 100% | 32% | 63% | 5% |

EXAMPLE III

A reaction flask was charged with 20 grams of 2,6-dichloropyridine and 150 grams of pyridine and agitated moderately. After all the 2,6-dichloropyridine was dissolved, 50 grams of 50 percent caustic (NaOH) aqueous solution and 19 grams of zinc dust were added. The reaction was maintained at about 50°C and 1 atmosphere pressure and samples of liquid taken periodically and analyzed by vapor phase chromatography as follows:

| Reaction time hours | Conversion of 2,6-dichloropyridine | Yields | | |
|---|---|---|---|---|
| | | 2-Chloropyridine | Pyridine | Others |
| 0.5 | 51% | 28% | 61% | 11% |
| 1 | 90% | 29% | 59% | 12% |
| 2 | 99.8% | 29% | 56% | 15% |
| 3 | 99.9% | 29% | 58% | 14% |

What is claimed is:

1. A process for preparing 2-chloropyridine consisting essentially of reacting together in the liquid phase at a temperature in the range of −10°C. to 100°C., 2,6-dichloropyridine at least 0.25 gram-atoms per mole of 2,6-dichloropyridine of a finely divided metal selected from the group consisting of zinc, iron, cobalt and aluminum and at least 0.1 part by weight per part by weight of said 2,6-dichloropyridine of a base selected from the group consisting of an alkali metal hydroxide and an alkaline earth metal hydroxide.

2. The process of claim 1 wherein a pressure of from about 0.2 atmosphere to about 100 atmospheres is employed.

3. The process of claim 2 wherein said metal is selected from the group consisting of zinc and iron.

4. The process of claim 3 wherein said alkali metal hydroxide is selected from the group consisting of sodium hydroxide, potassium hydroxide, lithium hydroxide, cesium hydroxide and rubidium hydroxide and said alkaline earth metal hydroxide is selected from the group consisting of calcium hydroxide and magnesium hydroxide.

5. The process of claim 4 wherein said metal is zinc.

6. The process of claim 5 wherein said base is provided as an aqueous solution containing up to about 75 percent by weight of said alkali metal hydroxide or said alkaline earth metal hydroxide and wherein at least 0.1 part by weight of said hydroxide per part by weight of 2,6-dichloropyridine is used.

7. The process of claim 6 wherein said zinc metal is in the form of zinc dust and said base is sodium hydroxide.

8. The process of claim 7 wherein pyridine is employed as a solvent.

9. The process of claim 8 wherein said reaction temperature is from about 0 to about 30°C, said pressure is from about 1 to about 10 atmospheres, said aqueous solution contains about 10 to about 53 percent by weight of sodium hydroxide, from about 1 to about 10 parts by weight of said sodium hydroxide per part by weight of 2,6-dichloropyridine is used and at least 0.25 gram-atoms of said zinc per mole of 2,6-dichloropyridine is used.

* * * * *